United States Patent [19]
Heinrich et al.

[11] Patent Number: 4,966,621
[45] Date of Patent: Oct. 30, 1990

[54] FINELY DISPERSED LIQUID PLANT PROTECTION AGENTS

[75] Inventors: Rudolf Heinrich; Konrad Albrecht, Kelkheim, both of Fed. Rep. of Germany

[73] Assignee: Hoechst Aktiengesellschaft, Frankfurt am Main, Fed. Rep. of Germany

[21] Appl. No.: 57,482

[22] Filed: Jun. 3, 1987

Related U.S. Application Data

[63] Continuation of Ser. No. 883,859, Jul. 10, 1986, which is a continuation of Ser. No. 578,282, Feb. 8, 1984, abandoned.

[30] Foreign Application Priority Data

Feb. 11, 1983 [DE] Fed. Rep. of Germany ....... 3304677
Dec. 23, 1983 [DE] Fed. Rep. of Germany ....... 3346637

[51] Int. Cl.$^5$ ............................................. A01N 57/12
[52] U.S. Cl. ............................................. 71/86; 71/108; 71/79; 71/DIG. 1; 252/351
[58] Field of Search ................... 71/79, 116, DIG. 1, 71/108, 86; 252/351

[56] References Cited

U.S. PATENT DOCUMENTS

| | | | |
|---|---|---|---|
| 3,285,816 | 11/1966 | Kaplan et al. | 252/351 |
| 3,462,520 | 8/1969 | Nehmsman et al. | 252/351 |
| 3,658,959 | 4/1972 | Inks | 514/481 |
| 3,954,442 | 5/1976 | Becker et al. | 71/116 |
| 4,188,202 | 2/1980 | Gillings et al. | 71/DIG. 1 |

FOREIGN PATENT DOCUMENTS

| | | |
|---|---|---|
| 1959478 | 11/1969 | Fed. Rep. of Germany . |
| 368836 | 9/1980 | Fed. Rep. of Germany . |
| 1286699 | 8/1972 | United Kingdom . |
| 2082914A | 9/1981 | United Kingdom . |

OTHER PUBLICATIONS

Tamura et al., "Polyester Composition", CA 80 16263a, (1974).
Sasse, K., "Phosphoric Acid Deriv.", Houben-Weyl, Methoden der Organ. Chemie, vol. 12, part 2, pp. 143, 156–157, (1964).
Derwent Abstract, Week E39, Nov. 24, 1982.

Primary Examiner—Richard L. Raymond
Assistant Examiner—A. A. Owens
Attorney, Agent, or Firm—Curtis, Morris & Safford

[57] ABSTRACT

Aqueous emulsions of a plant protective agent such as a pesticide dispersed in the presence of a phosphate ester of a block copolymer of (1) ethylene and propylene oxides or (2) of an ethoxylated/propoxylated fatty alcohol.

7 Claims, No Drawings

FINELY DISPERSED LIQUID PLANT PROTECTION AGENTS

This application is a continuation of application Ser. No. 883,859, filed July 10, 1986, which is a continuation of application Ser. No. 578,282, filed Feb. 8, 1984, now abandoned.

The invention relates to concentrated, finely dispersed, liquid active compound formulations which are stable in use, contain the active compound in liquid form, are substantially free from troublesome inorganic salts, and, in the form described in the invention, or as a mixture with other finely dispersed, liquid formulations, can be diluted as desired with water.

It is known that pesticidal active compounds can be formulated in organic solvents, predominantly aromatics, with emulsifiers to give so-called emulsifiable concentrates (EC). It is also known that water-soluble pesticidal active compounds can be formulated in an aqueous medium with emulsifiers and, if required, other formulation assistants.

The formulation of pesticidal and, in particular, herbicidal active compounds from the group comprising the 2,6-dinitroaniline derivatives in the form of aqueous emulsions which contain 10 to 75% by weight of a herbicide, 0 to 60% by weight of an essentially water-immiscible solvent, 0.5 to 10% by weight of an emulsifier and 15 to 70% by weight of a 15% strength aqueous solution of an inorganic salt is also known, and is described in German Offenlegungsschrift No. 2,805,251.

However, the addition of the stated amounts of inorganic salts can, in practice, lead to problems through corrosion, or to flocculation, if these formulations are combined with other pesticidal formulations and it is necessary to employ only small amounts of water.

The preparation of concentrated aqueous emulsions, having a long shelf life, of herbicidal phenoxyalkanecarboxylates using ester-soluble emulsifiers and water-soluble dispersants is also known, and is described in European Patent Application No. 47396. The ester-soluble emulsifiers used, if necessary as a mixture with alkylarylsulfonates, are fatty acid polyethylene glycol esters, polyethylene glycol ethers of fatty alcohols, of glycerides or of alkylphenols, and polyoxyethylene and polyoxypropylene block polymers. The dispersants used are phosphated alkylaryl polyethylene oxides which contain ammonium, sodium or potassium salts of phosphorylated polystyrylphenyl polyethylene oxide or ethylene oxide condensates of fatty amines.

The amounts of oil-soluble emulsifiers added are between 1.01 and 11.1 parts by weight per 100 parts by weight of phenoxyalkanecarboxylic acid ester. The amounts of dispersants are 0.5 to 5 parts by weight per 100 parts by weight of aqueous solution. To avoid the foam formation which takes place, antifoams based on long-chain alcohols and silicones are added.

Attempts to extend the use of the above-mentioned water-soluble ammonium, sodium or potassium salts of phosphorylated alkylaryl polyethylene oxides to active compounds other than those mentioned in European Patent Application No. 47396 led to considerable problems in respect of performance characteristics. In storage tests over a period of three months at 50° C., a number of formulations exhibited demulsification, which was reversible only under certain circumstances.

Similar results were obtained with the salts of phosphorylated polystyrylphenyl polyethylene oxides (R-Soprophor FL), which salts were used, in European Patent Application No. 33291, for the preparation of concentrated oil-in-water emulsions, as well as with the alkylaryl polyglycol ether compounds mentioned in German Offenlegungsschrift No. 3,111,934, which, even in combination with alkylarylsulfonic acid salts, gave colloidal emulsions which were heat-stable only under certain circumstances.

The dispersants polyvinyl alcohol and gum arabic used in German Offenlegungsschrift No. 3,009,944 for the formulation of insecticidal phosphates led to significant demulsification phenomena or to phase separation during storage at 50° C., even for slight pH variations. The addition of electrolytes, as is usual when buffer mixtures are used or for improving the low-temperature stability, caused coagulation and precipitation.

European Patent Application No. 28052 describes a process for the preparation of aqueous free-flowing concentrates of the herbicide napropamide (N,N-diethyl-2-(1-naphthyloxy)-propionamide) with the aid of clays, nonionic emulsifiers, dispersants based on a ligninsulfonate and antifreezes. However, this process has the disadvantage that the viscosity varies sharply, depending on the storage temperatures and use temperatures. At elevated temperatures, the low viscosity can lead to sedimentation and phase separation.

Furthermore, other processes are known in which, similarly to European Patent Applications No. 17001, No. 9626 or No. 52313, the formulation components are comminuted beforehand in a dry-grinding mill and/or brought to the desired final particle size in a wet-grinding mill. However, these processes require additional expensive milling processes with all the disadvantages for dispersions.

It was therefore the object of the present invention to overcome the disadvantages of the pesticide formulations hitherto known, which contain solvents, inorganic salts or thickeners of mineral origin. A particular problem in this case was to provide concentrated, finely dispersed liquid pesticide formulations which are also stable at −10° C., contain the active compound in liquid form, are completely or substantially free from organic solvents, do pot contain any troublesome inorganic salts, are resistant to hydrolysis and, alone or as a mixture with other finely dispersed liquid formulations, can be diluted as desired with water.

It has now been found, surprisingly, that certain wetting agents and dispersants which are soluble in water and organic solvents can be more effectively and substantially more advantageously employed than the water-soluble dispersants of the phosphorylated alkylaryl polyethylene oxide type which are described in European Patent Application No. 47396.

Thus, it has been found that phosphorylated block copolymers based on propylene oxide and ethylene oxide or their salts, in contrast to the dispersants of the stated European Patent Application, give formulations which arc stable in use and have the above-mentioned advantageous properties.

These formulations are substantially free of inorganic salts and can also be used for other pesticides. By varying the polyethylene glycol content, the desired viscosity of the ready-prepared formulation can be established without difficulty, so that it is possible to dispense with the dispersants and thickeners of mineral origin which are otherwise used.

The process according to the invention is suitable both for the 2,6-dinitroaniline derivatives formulated in accordance with German Offenlegungsschrift No. 2,805,251 and for the herbicidal phenoxyalkanecarboxylates prepared in accordance with European Patent Application No. 47396. Likewise, using the present process, it is possible to obtain formulations, which are stable in use, of fungicides, as well as of insecticides, of acaricides and nematocides or of pheromones (insect attractants) and of so-called repellents. Moreover, active compounds which are used in the hygiene sector, such as disinfectants, can also be formulated using the process according to the invention.

The present invention therefore relates to plant protection agents based on aqueous emulsions, containing one or more active compounds, in particular a pesticide, a repellent or a pheromone, which contain, as oil-soluble and water-soluble dispersants, phosphorylated block copolymers based on propylene oxide and ethylene oxide, which, if appropriate, have a fatty alcohol nucleus, or alkali metal, alkaline earth metal, ammonium, mono-, di-or trialkylammonium or mono-, di- or trialkanolammonium salts thereof.

The mono-, di- and trialkyl- or -alkanolammonium salts have, in particular, 1 to 5 C atoms in the alkyl moiety.

These aqueous emulsions can additionally contain other conventional dispersants, emulsifiers, thickeners, diols or polyols as antifreezes and - particularly for solid active compounds - organic solvents.

Suitable phosphorylated block copolymers to be used according to the invention are the block polymers of the formula I

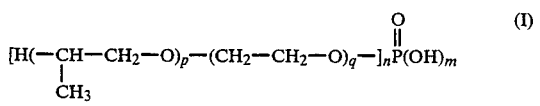

wherein
p denotes a number between 20 and 300,
q denotes a number between 10 and 300 and
n and m denote 1 or 2, and the sum n+m must be 3 or the block polymers of the formula II

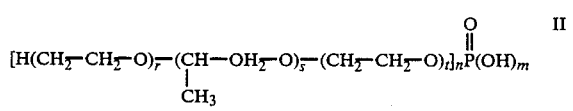

wherein
r and s independently of one another denote a number between 20 and 300,
t denotes a number between 10 and 300 and
n and m denote 1 or 2, and the sum n+m must be 3, or the block polymers having a fatty alcohol nucleus, of the formula III

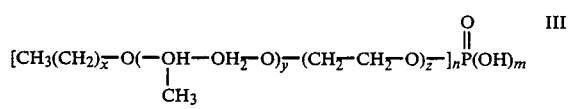

wherein
x denotes a number between 10 and 30,
y denotes a number between 5 and 100,
z denotes a number between 5 and 100 and
n and m denote 1 or 2, and n+m must be 3.

The block polymers given in the formulae, or their salts, can be employed individually or as a mixture.

In formula (I), p preferably denotes a number between 50 and 200 and q preferably denotes a number between 30 and 200. In formula II, r preferably denotes a number between 30 and 200, s denotes a number between 50 and 200 and t denotes a number between 30 and 200.

Among the above-mentioned block polymers, the polymers of formula II are particularly suitable.

Suitable diols or polyols which can be used as antifreezes are ($C_2$–$C_5$) alkane diols, in particular ethylene glycol or butane diol, ($C_3$–$C_5$) alkane triols, in particular glycerol, and polyethylene glycols having various molecular weights, and alkylglycols, in particular ($C_1$–$C_4$) alkylglycols.

When solid active compounds are used, it is critical that the active compounds have moderate to very good solubility in the organic solvents used. The active compounds should be insoluble or only slightly soluble in water.

Examples of suitable active compounds are the herbicides
(a) methyl$\alpha$-4-(2',4'-dichlorophenoxy)-phrnoxypropionate [common name: illoxan]
(b) ethyl 2-[4-(6-chloro-2-benzothiazolyloxy)-phenoxy]-propionate,
(c) ethyl 2-[4-(6-chloro-2-benzoxazolyloxy)-phenoxy]-propionate,
(d) 2,6-dinitro-4-trifluoromethyl-N,N-dipropylaniline [common name: trifluralin],
(e) 2,6-dinitro-4-isopropyl-N,N-dipropylaniline [common name: isopropalin]
(f) 2,6-dibromo-4-hydroxybenzonitrile octanoate and
(g) 2-sec.-butyl-4,6-dinitrophenol [common name: dinoterb]
the insecticides
1,4,5,6,7,7-hexachloro-8,9,10-trinorborn-5-en-2,3-ylenedimethyl sulfite [common name: endosulfan]and
2-(1-methyl-n-propyl)-4,6-dinitrophenyl 2-methylcrotonate [common name: binapacryl],
the pheromones
(E)-8-(E)-10-dodecadienol and
(Z)-7,8-epoxy-2-methyl-octadecane,
and the repellent
(a) dimethyl phthalate.

The herbicides (a), (d), (e), (f) and (g), the above-mentioned insecticides and the repellent are disclosed in H. Martin, Pesticide Manual 6th edition 1979. The herbicides (b) and (c) are described in German Offenlegungsschrift No. 2,640,730, and the two pheromones are described in M. Beroza, Chem. Controlling Insect Behavior, Academic Press, N.Y. 1970.

Conventional dispersants to be employed if necessary are, preferably, lignin sulfonates, Na salts of dinaphthylmethanedisulfonic acids, the Na salt of a sulfonic acid obtained from cresol, formaldehyde, Na sulfite and hydroxynaphthalenesulfonic acid, the Na salt of a sulfonic acid obtained from m-cresol, formaldehyde and Na sulfite, condensation products obtained from arylsulfonic acids and formaldehyde Na salt, triethanolamine salts of phosphorylated polystyrylphenyl polyethylene oxides, polyvinyl alcohol, calcium dodecylbenzenesulfonate and alkylnaphthalenesulfonates having various alkyl chain lengths.

Suitable emulsifiers are non-ionic, anionic or cationic surface-active substances, mixtures of non-ionic components with anionic components being predominantly used. However, it is also possible to use combinations of non-ionic and cationic surfactants. The emulsifiers which are preferably employed include calcium phenylsulfonate, ethoxylated nonylphenols, ethoxylated aliphatic alcohols, ethoxylated castor oil, propylene glycol ethylene glycol block polymers and mixtures of these.

Water-soluble polymers, such as, for example, polyvinyl alcohol, polyvinylpyrrolidone and cellulose derivatives, can be used as thickeners.

Suitable organic solvents are all water-immiscible solvents, for example aromatics, such as toluene, xylenes, 1- or 2-methylnaphthalene or dimethylnaphthalenes, aliphatics, such as paraffin oils, vegetable oils, alicyclic compounds, such as cyclohexane, alkanols, such as cyclohexanol or i-octyl alcohol, ethers, such as diethyl ether, ketones, such as cyclohexanone, 4-methylcyclohexanone or isophorone, and esters, such as ethyl acetate and tri-n-butyl phosphate.

The plant protection agents according to the invention contain, in particular, 5-60% by weight of active compound, 10-70% by weight of water, 0.5-20% by weight of phosphorylated block polymers, 0 to 50% by L weight of a diol or polyol, 0-10% by weight of a conventional dispersant, 0-15% by weight of emulsifiers, 0-10% by weight of thickeners and 0 to 30% by weight of an organic solvent.

The invention furthermore relates to a process for the preparation of the plant protection agents according to the invention, wherein the required amounts of the above-mentioned components are stirred or shaken at temperatures between 0° C. and 60° C., advantageously at room temperature, in a zone of high turbulence, until the desired stable emulsion has formed, the particle diameters preferably being brought to 1-15 μmicrons.

To carry out the process in practice, the aqueous phase (carrier phase) is first prepared by stirring the dispersant and, if required, the diols or polyols, into water. Thereafter, the emulsifier component is added to the active compound to be emulsified, and the active compound is finely dispersed in the aqueous phase. In the case of active compounds having a melting point of about 0° C. or above, it may be necessary to prepare concentrated solutions of these active compounds in one or more of the above-mentioned organic solvents, and, after the addition of emulsifiers and, if required, stabilizers, to disperse the solutions in the aqueous phase.

However, it is also possible first to mix the dispersant with the active compound and then to disperse these together in the aqueous phase.

Dispersing can be effected by means of a stirring process or, if appropriate, a shaking process, and is advantageously continued until the organic phase corresponds to the desired droplet size. A droplet diameter of 1-15 μmicrons is recommended. The dispersing process is advantageously carried out at room temperature, but can also be effected at low temperatures or at elevated temperatures.

The process is particularly suitable for those active compounds which, because of their low melting point, can be converted to a finely dispersed aqueous phase with the aid of milling apparatuses only with difficulty, if at all, or for those active compounds for which the milling process requires special safety precautions.

The examples which follow illustrate the invention:

EXAMPLE 1

36% by weight of methyl 2-(4-(2′,4′-dichlorophenoxy)-phenoxy)-propionate was dissolved in 18% by weight of xylene at 20-25° C., while stirring, and 8% by weight of a fatty acid polyglycol ester (containing 40 EO*) was added. 4% by weight of the potassium salt of the phosphorylated block copolymer of the above-mentioned formula I (with n=1 and an amount of 30% of polyethylene glycol in the end product) was dissolved in 24% by weight of water, likewise at room temperature, after which 10% by weight of ethylene glycol was added. The above-mentioned organic phase was allowed to run slowly into this aqueous phase, while stirring vigorously with a paddle stirrer, and the resulting white emulsion was stirred for about a further 15 minutes. A sample is stored for 3 months at 50° C.. The formulation was stable chemically as well as in use.
*EO=ethylene oxide unit

EXAMPLE 2

30% by weight of ethyl 2-(4-(6-chloro-2-benzothiazolyloxy)-phenoxy-propionate was dissolved in 20% by weight of xylene at 40-45° C., while stirring, and 6% by weight of the potassium salts of the phosphorylated block copolymers of the formula I (a mixture of the polymers with n=1 and n=2 in a ratio of 1:1, with a total amount of 40% of polyethylene oxide) and 2% by weight of the triethanolamine salt of a phosphorylated polystyryl phenyl polyethylene oxide and 4% by weight of calcium dodecylbehzenesulfonate were added.

9% by weight of ethylene glycol was dissolved in 29% by weight of water at room temperature. The above-mentioned organic phase was allowed to run into this aqueous solution, while stirring vigorously with a paddle stirrer, and the resulting white emulsion was stirred for about a further 15 minutes at room temperature. A sampler was stored for 3 months at 50° C. The formulation was stable chemically and in use.

EXAMPLE 3

30% by weight of 2,6-dinitro-4-trifluoromethyl-N,N-dipropylaniline (trifluralin) was dissolved in 15% by weight of xylene at 20°-25° C., while stirring, and 8% by weight of the triethanolamine salt of the phosphorylated block copolymer having a fatty alcohol nucleus of the above-mentioned formula III (a mixture of the polymers with n=1 and n=2 in a ratio of 1:1) and 2% by weight of the triethanolamine salt of a phosphorylated polystyrylphenyl polyethylene oxide and 4% by weight of a fatty acid polyglycol ester (36 EO) were added. 6% by weight of polyethylene glycol (molecular weight 500) was dissolved in 35% by weight of water at room temperature. The organic phase was allowed to run slowly into this aqueous solution, while stirring vigorously, and the resulting yellow emulsion was stirred for about a further 20-25 minutes, until the pale yellow shade of the emulsion no longer changed. The formulation was stable chemically and in use, even after storage at various temperatures.

EXAMPLE 4

22.3% by weight of technical-grade endosulfan was dissolved in 21% by weight of a mixture of aromatics (boiling range 219° C.-282° C.), while stirring, and 10% by weight of the triethanolamine salt of the phosphorylated block copolymer of the above-mentioned formula I (n=2 and an amount of 35% of polyethylene oxide in the end product) was added. 12% by weight of polyethylene glycol (molecular weight 1000) was dissolved in 34.7% by weight of water at room temperature. The organic phase was allowed to run slowly into this solution, while stirring vigorously, and the resulting beige-colored emulsion was stirred for about a further 15-20 minutes.

The formulation was stable chemically and in use.

EXAMPLE 5

30.8% by weight of 2-sec.-butyl-4,6-dinitrophenyl 3-methylcrotonate (binapacryl) is dissolved in 15% by weight of xylene, while stirring, and 5% by weight of the triethanolamine salt of a phosphorylated block copolymer of the above-mentioned formula I (with n=1) is added.

5% by weight of the calcium salt of the phosphorylated block copolymer having a fatty alcohol nucleus of the above-mentioned formula III (with n=2) and 4% by weight of a fatty acid polyglycol ester (40 EO) were dissolved in 33.2% by weight of water. Thereafter, 7% by weight of ethylene glycol was added, and stirring was continued. The above-mentioned organic phase was allowed to run into this aqueous solution at room temperature, while stirring vigorously with a paddle stirrer, and the resulting yellowish emulsion was stirred for about a further 15-20 minutes.

The formulation was stable chemically and in use.

EXAMPLE 6

40.4% by weight of dimethyl phthalate was mixed with 4.2% by weight of the triethanolamine salt of the phosphorylated block copolymer of the formula I (a mixture of the polymers with n=1 and n=2 in a ratio of 1:1, with a total amount of 40% of ethylene oxide).

10% by weight of ethylene glycol and 3.4% by weight of the potassium salt of the phosphorylated block copolymer having a fatty alcohol nucleus of the above-mentioned formula III (a mixture of the polymers with n=1 and n=2 in a ratio of 1:1) and 3% by weight of ethoxylated tridecyl alcohol (6 EO) were dissolved in 39.0% by weight of water. The above-mentioned organic phase was allowed to run into this aqueous solution at room temperature, while stirring vigorously with a paddle stirrer, and the resulting white emulsion was stirred for about a further 15-20 minutes.

The formulation was stable chemically and in use.

EXAMPLE 7

6.0% by weight of ethoxylated nonylphenol (6 EO), 7% by weight of the potassium salt of the phosphorylated block copolymer of the above-mentioned formula I (with n=1 and a total amount of 30% of ethylene oxide) and 10% by weight of glycerol were dissolved in 45% by weight of water. 32.0% by weight of (E)-8-(E)-10-dodecadienol was allowed to run into this solution, while stirring vigorously. The resulting white emulsion was stirred for a further 15 to 20 minutes.

The formulation was stable chemically and in use.

EXAMPLE 8

30% by weight of 2,6-dinitro-4-trifluoromethyl-N,N-dipropylaniline (trifluralin) was dissolved in 15% by weight of xylene at 20°-25° C., while stirring, and 3% by weight of a phosphorylated block copolymer of the above-mentioned formula II (a mixture of the polymers with n=1 and n=2 in a ratio of 1:1 being used, and r denoting 40-60, s denoting 69-90 and t denoting 30-60 in these polymers) and 10% by weight of a fatty acid polyglycol ester (36 EO) were added. 10% by weight of polyethylene glycol (molecular weight 500) was dissolved in 38% by weight of water at room temperature. The organic phase was allowed to run slowly into this aqueous solution, while stirring vigorously, and the resulting yellow emulsion was stirred for about a further 20-25 minutes, until the pale yellow shade of the emulsion no longer changed. The formulation was stable chemically and in use, even after storage at various temperatures.

EXAMPLE 9

20% by weight of ethyl'2-(4-(6-chloro-2-benzothiazolyloxy)-phenoxy-propionate was dissolved in 25% by weight of xylene at 40°-45° C., while stirring, and 6% by weight of the potassium salts of the phosphorylated block copolymers of the formula II of Example 1, and 2% by weight of the triethanolamine salt of a phosphorylated polystyrylphenyl polyethylene oxide and 4% by weight of calcium dodecylbenzenesulfonate, were added.

10% by weight of ethylene glycol were dissolved in 33% by weight of water at room temperature. The above-mentioned organic phase was allowed to run into this aqueous solution, while stirring vigorously with a paddle stirrer, and the resulting white emulsion was stirred for about a further 15 minutes at room temperature. A sample was stored for 3 months at 50° C. The formulation was stable chemically and in use.

EXAMPLE 10

36% by weight of methyl 2-(4-(2',4'-dichlorophenoxy)-phenoxy)-propionate was dissolved in 18% by weight of xylene at 20°-25° C., while stirring, and 6% by weight of a fatty acid polyglycol ester (with 40 EO) was added. 6% by weight of the potassium salt of the phosphorylated block copolymer of formula II, wherein n denotes 1, r denotes 100-130, s denotes 190-220 and t denotes 60-90, was dissolved in 24% by weight of water, likewise at room temperature, after which 10% by weight of ethylene glycol was added. The above-mentioned organic phase was allowed to run slowly into this aqueous phase, while stirring vigorously with a paddle stirrer, and the resulting white emulsion was stirred for about a further 15 minutes. A sample was stored for 3 months at 50° C. The formulation was stable both chemically and in use.

EXAMPLE 11

22.3% by weight of technical-grade endosulfan was dissolved in 21% by weight of a mixture of aromatics (boiling range 219° C.-282° C.), and 10% by weight of the triethanolamine salt of the phosphorylated block copolymer of the above-mentioned formula II, wherein n denotes L 2, r denotes 100-120, s denotes 190-220 and t denotes 6090, was added. 10% by weight of polyethylene glycol (molecular weight 1000) was dissolved in 36.7% by weight of water, at room temperature. The organic phase was allowed to run slowly into this solution, while stirring vigorously, and the resulting beige-colored emulsion was stirred for about a further 15-20 minutes. The formulation was stable chemically and in use.

EXAMPLE 12

40.4% by weight of dimethyl phthalate was mixed With 6.2% by weight of the triethanolamine salt of the phosphorylated block copolymer of the formula II of Example 1.

8% by weight of urea and 3.4% by weight of the potassium salt of a phosphorylated polystyrylphenyl polyethylene oxide and 3% by weight of ethoxylated tridecyl alcohol (6 EO) were dissolved in 39.0% by weight of water. The above-mentioned organic phase was allowed to run into this aqueous solution at room temperature, while stirring vigorously with a paddle stirrer, and the resulting white emulsion was stirred for about a further 15-20 minutes.

The formulation was stable chemically and in use.

EXAMPLE 13

30.8% by weight of 2-sec.-butyl-4,6-dinitrophenyl 3-methylcrotonate (binapacryl) was dissolved in 15% by weight of xylene, while stirring, and 5% by weight of the triethanolamine salt of the phosphorylated block copolymer of the above-mentioned formula II was added, a mixture of the polymers with n=1 and n=2 in a ratio of 1:2 being employed, and r denoting 90-120, s denoting 210-240 and t denoting 50-80 in these polymers.

5% by weight of the calcium salt of a phenylsulfonic acid and 4% by weight of a fatty acid polyglycol ester (40 EO) were dissolved in 33.2% by weight of water. Thereafter, 7% by weight of ethylene glycol was added, and stirring was continued. The above-mentioned organic phase was allowed to run into this aqueous solution at room temperature, while stirring vigorously with a paddle stirrer, and the resulting yellowish emulsion was stirred for about a further 15-20 minutes.

The formulation was stable chemically and in use.

EXAMPLE 14

6.0% by weight of ethoxylated nonylphenol (6 EO), by weight of the potassium salt of the phosphorylated block copolymer of the above-mentioned formula II (a mixture of the polymers with n=1 and n=2 in a ratio of 2:1 being used, and r denoting 40-60, s denoting 60-90 and t denoting 30-60 in these polymers) and 10% by weight of glycerol were dissolved in 45% by weight of water. 32.0% by weight of (E)-8-(E)-10-dodecadienol was allowed to run into this solution, while stirring vigorously. The resulting white emulsion was stirred for a further 15 to 20 minutes.

The formulation was stable chemically and in use.

What is claimed is:

1. An aqueous emulsion comprising 10 to 70 percent by weight of water, 5 to 60 percent by weight of a dispersed herbicide and, as a dispersant therefor, 0.5 to 20 percent by weight of at least one member selected from the group consisting of

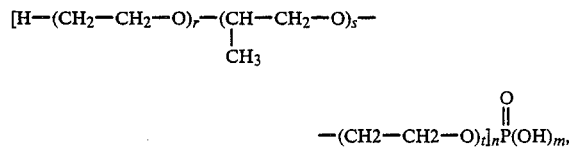

wherein
p is a number between 20 and 30 and
q is a number between 10 and 300;
block copolymer of the formula

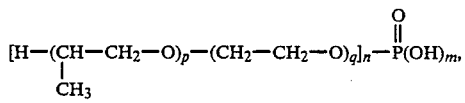

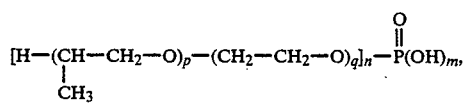

wherein
r and s are independently a number between 20 and 300 and
t is a number between 10 and 300,
where n and m in each of said formulas is 1 or 2 and the sum of n and m is 3; and
alkali metal, alkaline earth metal, ammonium, mono-, di-, and tri-alkyl ammonium, and mono-, di-, and tri-alkanolammonium salts of said block copolymers.

2. An aqueous emulsion as in claim 1 which additionally comprises at least one member selected from the group consisting of additional different dispersants, emulsifiers, thickeners, organic solvents, and diols and polyols.

3. An aqueous emulsion as in claim 2 which additionally comprises a diol or polyol which is a ($C_2$-$C_5$) alkanediol, a ($C_5$-$C_5$) alkanetriol, a polyethylene glycol, or an alkyl glycol.

4. An aqueous emulsion as in claim 3 wherein said diol or polyol is ethylene glycol, butane diol, or glycerol.

5. An aqueous emulsion as in claim 1 which additionally comprises 0 to 50 percent by weight of a diol or polyol, 0 to 10 percent by weight of an additional different dispersant, 0 to 15 percent by weight of an emulsifier, 0 to 10 percent by weight of a thickener, and 0 to 30 percent by weight of an organic solvent.

6. An aqueous emulsion comprising a herbicide, a dispersant which is a member selected from the group consisting
of block copolymers of the formula

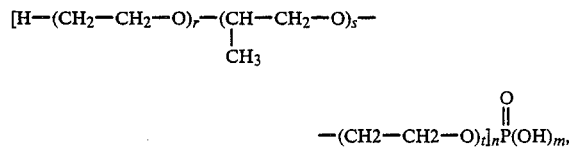

wherein
p is a number between 20 and 300 and
q is a number between 10 and 300;
block copolymers of the formula

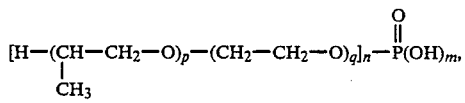

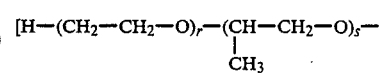

wherein
r and s are independently a number between 20 and 300 and
t is a number between 10 and 300,
where n and m in each of said formulas is 1 or 2 and the sum of n and m is 3; and
alkali metal, alkaline earth metal, ammonium, mono- and di-, and tri-alkyl ammonium, and mono-, di-, and tri-alkanolammonium salts of said block copolymers.

7. An aqueous emulsion as in claim 1 wherein said herbicide is methyl α-4-(2',4'-dichlorophenoxy)-phenoxypropionate.

* * * * *